(12) United States Patent
Klingenbeck

(10) Patent No.: US 9,031,295 B2
(45) Date of Patent: May 12, 2015

(54) ANGIOGRAPHIC METHOD FOR EXAMINING A VASCULAR SYSTEM

(71) Applicant: Klaus Klingenbeck, Aufsess (DE)

(72) Inventor: Klaus Klingenbeck, Aufsess (DE)

(73) Assignee: Siemens Aktiengesellschaft, München (DE)

( * ) Notice: Subject to any disclaimer, the term of this patent is extended or adjusted under 35 U.S.C. 154(b) by 99 days.

(21) Appl. No.: 13/963,265

(22) Filed: Aug. 9, 2013

(65) Prior Publication Data

US 2014/0044330 A1 Feb. 13, 2014

(30) Foreign Application Priority Data

Aug. 13, 2012 (DE) .................. 10 2012 214 351

(51) Int. Cl.
*G06K 9/00* (2006.01)
*A61B 6/00* (2006.01)
*A61B 6/03* (2006.01)

(52) U.S. Cl.
CPC .................. *A61B 6/486* (2013.01); *A61B 6/507* (2013.01); *A61B 6/032* (2013.01); *A61B 6/4441* (2013.01); *A61B 6/504* (2013.01); *A61B 6/5217* (2013.01)

(58) Field of Classification Search
USPC .................................................. 382/128–134
See application file for complete search history.

(56) References Cited

U.S. PATENT DOCUMENTS

| | | | |
|---|---|---|---|
| 5,150,292 A * | 9/1992 | Hoffmann et al. | 600/431 |
| 5,771,308 A * | 6/1998 | Florent | 382/130 |
| 5,991,697 A * | 11/1999 | Nelson et al. | 702/49 |
| 6,842,638 B1 * | 1/2005 | Suri et al. | 600/425 |
| 7,020,314 B1 * | 3/2006 | Suri et al. | 382/130 |
| 7,486,811 B2 * | 2/2009 | Kaufman et al. | 382/128 |
| 7,500,784 B2 | 3/2009 | Grebner et al. | |
| 8,706,196 B2 * | 4/2014 | Redel | 600/425 |
| 2001/0031920 A1 * | 10/2001 | Kaufman et al. | 600/431 |
| 2002/0176614 A1 * | 11/2002 | Kuth et al. | 382/128 |
| 2008/0009708 A1 * | 1/2008 | Machida | 600/414 |

(Continued)

FOREIGN PATENT DOCUMENTS

DE 102005008753 A1 8/2006

OTHER PUBLICATIONS

G. Reiter, U. Reiter, B. Kainz, A. Greiser, Bischof Horst, R. Rienmüller; "MR vector field measurement and visualization of normal and pathological time-resolved three-dimensional cardiovascular blood flow patterns"; J Cardiovasc Magn Reson 2007; vol. 9: pp. 237-238.

(Continued)

*Primary Examiner* — Alex Liew

(57) ABSTRACT

An angiographic method is provided. The method includes: identification of a relevant part in acquired angiography 4D sequences which exhibit a vascular disorder or change; determination of a centerline for the part; ascertainment of lines parallel and surrounding the centerline; specification of perpendicular cross-sections; determination of voxels; ascertainment of bolus curves as a function of time for each voxel; which intersects one of the cross-sections; determination of a time for each voxel; measurement of the true Euclidean distance between voxels at the positions along the centerline and the parallel lines; division of the measured distance by the time difference; determination of second speed components, running transversely, proportional to the relative change in mass for each voxel; and calculation of the blood flow in the relevant part of the vascular system on the basis of the speed components.

10 Claims, 4 Drawing Sheets

(56) References Cited

U.S. PATENT DOCUMENTS

| | | | |
|---|---|---|---|
| 2008/0187201 A1* | 8/2008 | Liang et al. | 382/131 |
| 2009/0016587 A1* | 1/2009 | Strobel et al. | 382/130 |
| 2009/0093703 A1* | 4/2009 | Silber | 600/410 |
| 2009/0105579 A1* | 4/2009 | Garibaldi | 600/409 |
| 2011/0274333 A1* | 11/2011 | Prevrhal et al. | 382/132 |
| 2013/0215388 A1* | 8/2013 | Imamura | 351/206 |
| 2014/0044330 A1* | 2/2014 | Klingenbeck | 382/130 |
| 2014/0086461 A1* | 3/2014 | Yao et al. | 382/128 |

OTHER PUBLICATIONS

Charles Anthony Mistretta, E. Oberstar, B. Davis, E. Brodsky, C.M. Strother; 4D-DSA and 4D Fluoroscopy: Preliminary Implementation; Proceedings of the SPIE—The International Society for Optical Engineering: 2010. vol. 7622, pp. 762227-1 to 762227-8 (8 pp.), Conference: San Diego, CA, USA, Feb. 15-18, 2010, Conference paper (English).

* cited by examiner

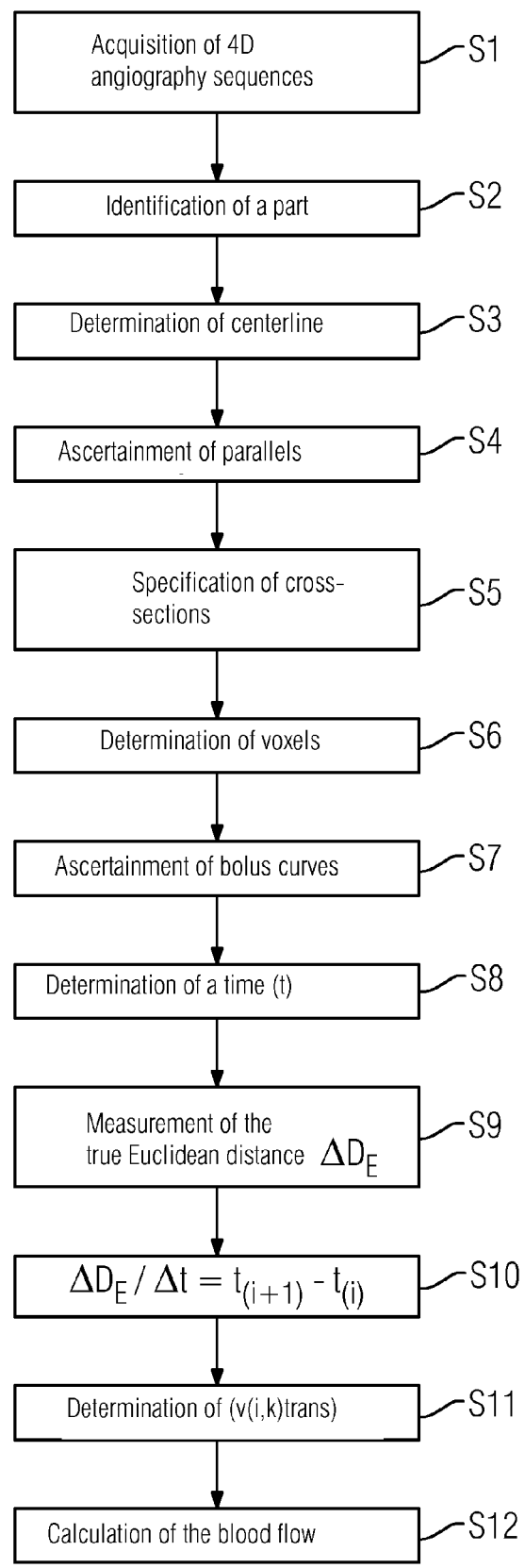

ANGIOGRAPHIC METHOD FOR EXAMINING A VASCULAR SYSTEM

CROSS REFERENCE TO RELATED APPLICATIONS

The present application claims priority to German Office application No. 1020 12214351.3 DE filed Aug. 13, 2012, the entire content of which is hereby incorporated herein by reference.

FIELD OF INVENTION

The invention relates to an angiographic method for examining a vascular system of an object under examination in order to determine flow characteristics inside vessels.

BACKGROUND OF INVENTION

4D DSA imaging is a new promising imaging method which can be used to represent the spatiotemporal diffusion of the blood whilst using contrast agent inside a 3D vascular tree.

The 4D DSA imaging method has been described for example by Prof. Dr. Charles A. Mistretta et al. in "4D-DSA and 4D Fluoroscopy: Preliminary Implementation", published in Proceedings of the SPIE, 2010, Vol. 7622, pp. 762227-1 to 8. In the case of the 4D DSA approach, the dynamic behavior of the contrast agent in the vessels is extracted from the rotational angiography projections and said behavior is superimposed by means of perspective back projection in a static 3D image of the vascular tree. In this situation, a time-resolved series of 3D data sets is produced; associated with each point in time in this series is a volume data set which represents the filling of the vascular tree with contrast agent at the respective point in time.

Such 4D DSA imaging methods are used in order to visualize the blood flow in a vessel section or vessel segment of a blood vessel, which contains a pathological, in other words an abnormal change. Such a pathological change in the vessel section is present for example in the form of an aneurysm, in other words an abnormal, locally limited, often voluminous extension. An aneurysm can occur in particular in a blood vessel in the area of the brain or the heart; the occurrence of an aneurysm is however in general not restricted to a specific body region. The clinical significance of an aneurysm which for example is localized in the brain consists in particular in the danger of a rupture, in other words a tearing or splitting, which can for example result in bleeding and thromboses. In medicine today the dynamics of the blood flow in an aneurysm are frequently considered to be an important factor for the pathogenesis of the aneurysm, in other words for its origin and development.

An angiography system for carrying out such a 4D DSA imaging method is known for example from U.S. Pat. No. 7,500,784 B2, which is described with reference to FIG. 1.

FIG. 1 shows a monoplanar X-ray system illustrated as an example having a C-arm 2 held by a stand 1 in the form of a six-axle industrial or jointed arm robot, at the ends of which C-arm 2 are mounted an X-ray source, for example an X-ray emitter 3 having an X-ray tube and collimator, and an X-ray image detector 4 as the image recording unit.

By means of the jointed arm robot known for example from U.S. Pat. No. 7,500,784 B2 which preferably has six axes of rotation and thus six degrees of freedom, it is possible to spatially adjust the C-arm 2 as desired, for example by rotating it around a rotation center between the X-ray emitter 3 and the X-ray detector 4. The angiographic X-ray system 1 to 4 according to the invention can be rotated in particular around rotation centers and axes of rotation in the C-arm plane of the X-ray image detector 4, preferably around the center point of the X-ray image detector 4 and around axes of rotation intersecting the center point of the X-ray image detector 4.

The known jointed arm robot has a base frame which is fixedly mounted for example on a floor. Attached thereon is a carousel capable of rotation around a first axis of rotation. On the carousel is attached a robot rocker capable of swiveling around a second axis of rotation, to which is affixed a robot arm capable of rotation around a third axis of rotation. At the end of the robot arm is attached a robot hand capable of rotation around a fourth axis of rotation. The robot hand has a retaining element for the C-arm 2, which is capable of swiveling around a fifth axis of rotation and is capable of rotation around a sixth axis of rotation running perpendicular to the latter.

The implementation of the X-ray diagnostic device is not dependent on the industrial robot. Normal C-arm units can also be used.

The X-ray detector 4 can be a rectangular or square, flat semiconductor detector which is preferably produced from amorphous silicon (a-Si). Integrating and possibly counting CMOS detectors can however also be used.

A patient 6 to be examined is situated in the beam path of the X-ray emitter 3 on a table surface 5 of a patient support table as the object under examination. Connected to the X-ray diagnostic device is a system control unit 7 having an imaging system 8 which receives and processes the image signals from the X-ray image detector 4 (control elements are for example not illustrated). The X-ray images can then be viewed on displays of a monitor rack 9. A processing unit 10, the function whereof will be described in more detail, is furthermore provided in the system control unit 7.

Instead of the X-ray system illustrated for example in FIG. 1 having the stand 1 in the form of the six-axle industrial or jointed arm robot, the angiographic X-ray system can also have a normal ceiling- or floor-mounted fixture for the C-arm 2.

Instead of the C-arm 2 illustrated by way of example, the angiographic X-ray system can also have separate ceiling- and/or floor-mounted fixtures for the X-ray emitter 3 and the X-ray detector 4 which for example are rigidly coupled electronically.

In order to acquire 4D angiography sequences, a rotational angiogram is first produced using the monoplanar X-ray system illustrated in FIG. 1 and from this is reconstructed the 3D vascular tree of the vessels filled with contrast agent. In order to capture the time components, 2D DSA sequences of the vessels filled with contrast agent are produced and back projected into the reconstructed 3D vascular tree.

For a better understanding of the production of the 2D DSA sequences, a time-intensity curve or contrast-intensity curve for a vessel section with characteristic values drawn in is illustrated by way of example in FIG. 2, wherein the blood flow is plotted as intensity I over the time t. After a noise-type progression of the bolus curve 11 of the contrast agent, the intensity I increases up to the intensity maximum 12 ($I_{max}$) in order to then drop away again to a mean noise level 13. The bolus curve 11 is furthermore characterized by its full width at half maximum (FWHM) 14 which lies between the mean rise and the mean fall of the bolus curve 11.

The arrival time 15 ($T_{rise}$) is the time which elapses up to the occurrence of the contrast agent bolus at the examined location and thus up to the rise of the bolus curve 11. The mean rise time 16 ($T_{rise,FWHM}$) is the time which elapses up to the occurrence of the full width at half maximum 14 of the bolus curve 11, in other words until the bolus curve 11 has reached the half of the intensity maximum 12 ($I_{max}$). The time up to the intensity maximum 12 ($I_{max}$) is referred to as maximum time 17 ($t_{max}$, time to maximum). The rise time 18 or wash-in time ($t_{wash\ in}$) denotes the steep rise of the bolus curve 11. The fall of the bolus curve 11 is denoted by the fall time 19 or wash-out time ($t_{wash\ out}$). The duration of the contrast agent bolus is denoted by the bolus or maximum time 20 ($t_{peak}$).

In the case of the 4D DSA imaging method the 3D vascular tree is therefore firstly reconstructed from a rotational angiogram of the vessels filled with contrast agent and reproduced completely intensified or enhanced in the stationary state of opacity. The dynamic propagation of the contrast agent in the 3D vascular tree is then captured from a series of 2D DSA recordings in a wash-in or wash-out phase, which is back projected into the reconstructed 3D volume.

In this situation, the acquisition of the 4D angiography sequences can take place from projections of a rotational angiogram on the basis of superimpositions by means of perspective back projection in a static 3D image of the vascular tree. In this situation, a time-resolved series of 3D data sets is produced; associated with each point in time in said series is a volume data set which represents the filling of the vascular tree with contrast agent at the respective point in time.

SUMMARY OF INVENTION

The object of the invention is to design an angiographic method for examining a vascular system of the type mentioned in the introduction in such a manner that as precise a determination as possible of flow characteristics inside vessels and representation of the spatiotemporal diffusion of the blood whilst using contrast agent can take place.

The object is achieved according to the invention for an angiographic examination method of the type mentioned in the introduction by the features described in claim 1. Advantageous developments are set down in the dependent claims.

The object is achieved according to the invention for an angiographic method for examining a vascular system of an object under examination in order to determine flow characteristics inside vessels by the following steps:

S1) acquisition of 4D angiography sequences,
S2) identification of at least one relevant part of the vascular system in the 4D angiography sequences which can exhibit a vascular disorder or change,
S3) determination of a centerline for said part,
S4) ascertainment of parallel lines which run parallel to the centerline and surround the centerline,
S5) specification of perpendicular cross-sections at least at positions which can be determined or chosen along the centerline,
S6) determination of voxels lying on the perpendicular cross-sections,
S7) ascertainment of bolus curves as a function of time for each voxel which intersects one of the cross-sections,
S8) determination of a time (t) for each of said voxels,
S9) measurement of the true Euclidean distance ($\Delta D_E$) between voxels at the positions along the centerline and the parallel lines,
S10) division of said measured distance ($\Delta D_E$) by the time difference ($\Delta t = t_{(i+1)} - t_{(i)}$) in order to obtain the amplitude of a first speed component of the blood flow speed in each of said voxels,
S11) determination of second speed components, running transversely (v(i, k)trans), proportional to the relative change in mass of the blood in the voxels, for each of said voxels and
S12) calculation of the blood flow in the relevant part of the vascular system on the basis of the speed components.

On the basis of said calculations a precise vector is obtained for the blood flow speeds in each voxel to enable exact imaging of 4D DSA sequences.

In an advantageous manner the acquisition of 4D angiography sequences can take place in accordance with step S1) from rotational angiography projections which are superimposed by means of perspective back projection in a static 3D image of the vascular tree. In this situation, a time-resolved series of 3D data sets is produced; associated with each point in time in said series is a volume data set which represents the filling of the vascular tree with contrast agent at the respective point in time.

It has proved to be advantageous if the calculation of the second speed components, running transversely (v(i, k)trans), takes place in accordance with method step S11) according to the formula:

$$v(i, k)\text{trans} \frac{m(i+1, k_+) - m(i, k_+)}{m(i, k) - m(i+1, k)}.$$

According to the invention, in accordance with step S8) the time (t) can be the maximum time ($t_{max}$), the rise time ($t_{wash\ in}$) of the wash-in phase and/or the fall time ($t_{wash\ out}$) of the wash-out phase of the bolus curve.

In an advantageous manner, after calculation of the first speed component for each voxel (i, j) it is possible in accordance with method step S10) to examine all adjacent voxels (k+) as to whether relative changes exist in the masses m(i+1, k+) to m(i, k+), and only then can the transversely running speed component (v(i, k)trans), which exhibits a value proportional to the relative change in mass, be determined in order to determine second speed components in accordance with method step S11) for a voxel (i, k).

BRIEF DESCRIPTION OF THE DRAWINGS

The invention will be described in detail in the following with reference to exemplary embodiments illustrated in the drawing. In the drawings:

FIG. 4 shows the conditions present in a cross-section of a vessel by way of explanation of the invention and FIG. 5 shows the sequence according to the invention of an angiographic examination method.

DETAILED DESCRIPTION OF INVENTION

Figure 3:
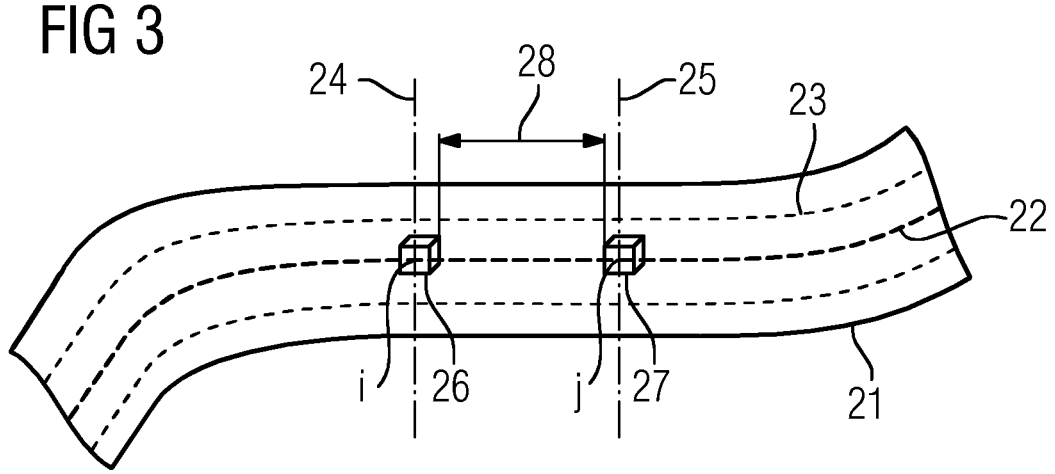
FIG. 3 shows the conditions present in a vessel by way of explanation of the invention.

The proposed angiographic examination method according to the invention firstly identifies the 3D vascular tree or relevant parts thereof. A relevant part could be a vessel section 21 illustrated in FIG. 3 or a branch, which can exhibit a vascular disorder such as an aneurysm or a significant stenosis.

In a second step the centerline 22 is determined for said part, the vessel section 21, and additional parallel lines 23 which run parallel to the centerline 22 and surround the centerline 22 are ascertained or set.

Next, several positions i and j are determined along the centerline 22. To this end the perpendicular cross-sections 24 and 25 respectively through the vessel section 21 are ascertained. In said positions i and j on the centerline 22 and on said perpendicular cross-sections 24 and 25 respectively are situated small volume elements, voxels (i) 26 or (j) 27. The voxel (i) 26 is indicated schematically at position i and the voxel (j) 27 at position j in FIG. 2.

Figure 1:
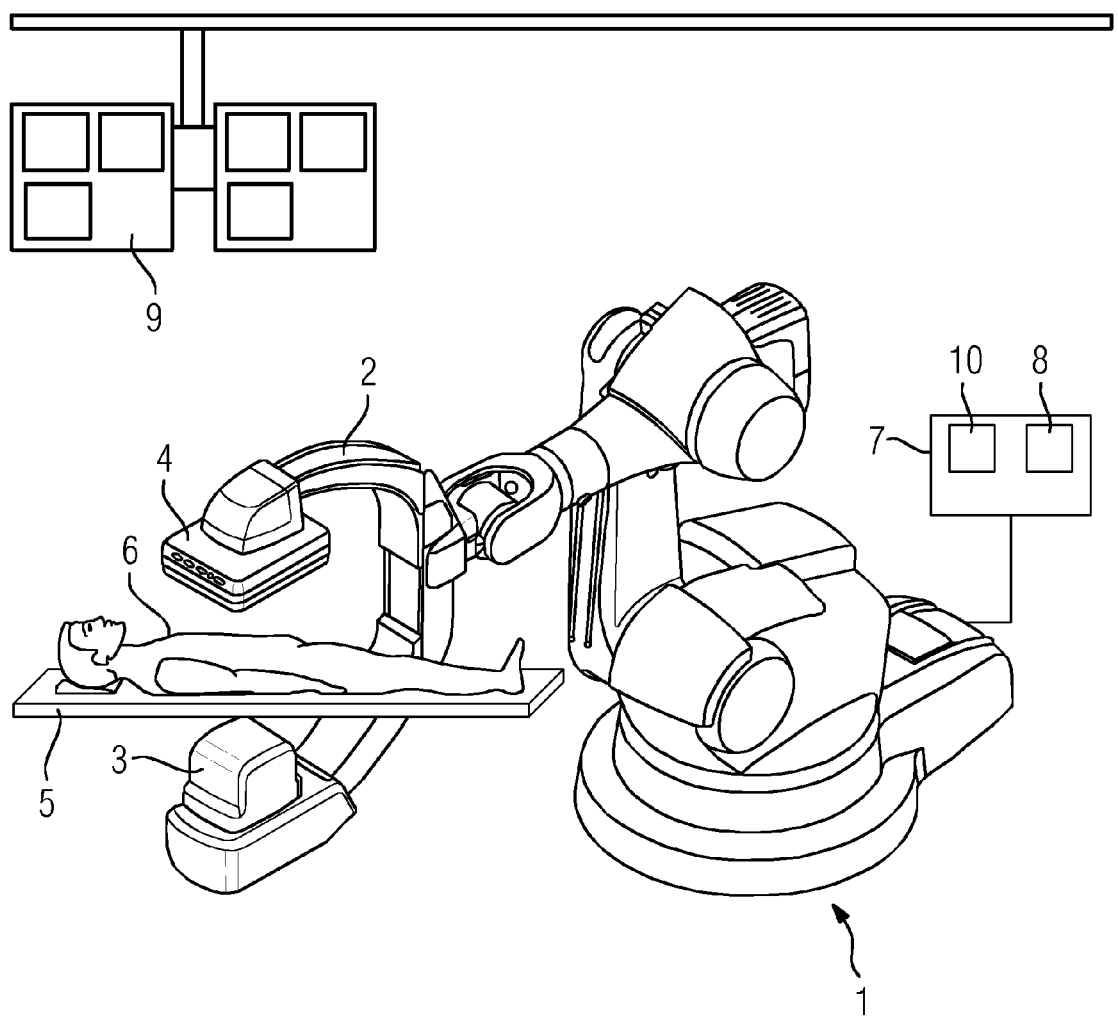
FIG. 1 shows a known C-arm angiography system having an industrial robot as the carrying device.
Figure 2:
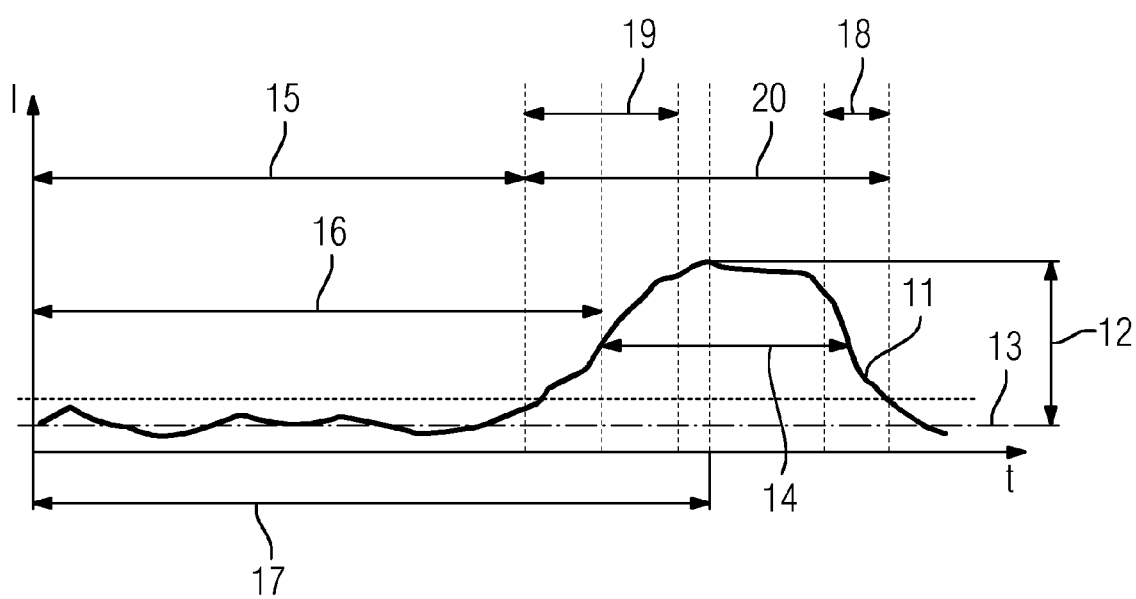
FIG. 2 shows a contrast-intensity curve with characteristic values drawn in by way of explanation of the invention.

For each voxel (i) 26 or (j) 27 which intersects a cross-section 24 or 25 respectively a time-intensity curve or contrast-intensity curve is now determined as a function of the time t in accordance with FIG. 2.

Figure 4:
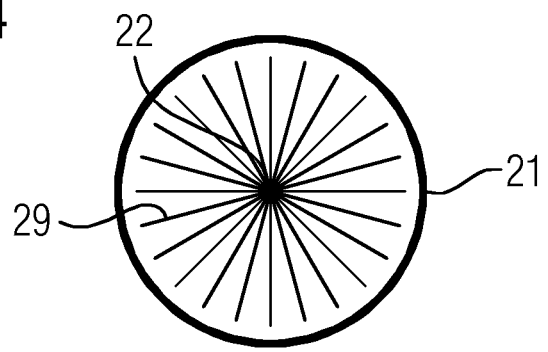

A cross-section 24 through the vessel section 21 is illustrated by way of example in FIG. 4, in which radial lines 29 emanate from the centerline 22. The parallel lines 23 are for example distributed equidistantly on said radial lines 29.

Parameter Definition:

Several parameters of the bolus curve 11, such as maximum time 17 ($t_{max}$, time to maximum), rise time 18 ($t_{wash\ in}$) in the wash-in phase and fall time 19 ($t_{wash\ out}$) in the wash-out phase, can be considered and used for further processing operations. In the following the maximum time 17 ($t_{max}$) at which the intensity maximum 12 of the bolus curve 11 occurs is considered as an example and denoted only as time t for the sake of simplicity.

In a position i said time t is now determined for all voxels 26 in the cross-section 24. Next, the same is done in the position j (i+1) or any other desired position in the cross-section 25 for all voxels 27. The times t(i) and t(i+1) for all voxels 26 or 27 concerned are the result obtained. The true Euclidean spacing or the true Euclidean distance $\Delta D_E$ 28 between the positions i and j (i+1) in the 3D space is measured along the centerline 22 and the parallel lines 23. By dividing said Euclidean distance $\Delta D_E$ 28 measured along the centerline 22 and/or the parallel lines 23 by the time difference $\Delta t = t_{(i+1)} - t_{(i)}$ of the occurrence of the contrast agent event at the respective voxels 26 or 27, the amplitude of the blood flow speed in each voxel 26 or 27 is obtained.

In this manner, speed components parallel to the lines 22 and 23 are obtained, for example the even flow. In reality however turbulent flows are produced at obstacles such as stenoses, aneurysms or other abnormalities of the vessel wall. For a precise determination of the flow it is also necessary to ascertain the speed components running transversely parallel to the perpendicular cross-sections 24 or 25.

For this purpose the area m(i, k) beneath the contrast-intensity curve or the bolus curve 11 is considered for the voxel (k) in the section (i) (cross-section 24), which is proportional to the mass of the blood. Alternatively, the maximum of the bolus curve 11 can be taken as another assessment. m(i, k) is now compared with m(i+1, k).

Now if m(i+1, k) is smaller than m(i, k), then a flow running transversely from the voxel k (26) must have been present. All adjacent voxels k+ (26) are therefore observed as to whether m(i+1, k+) has increased relative to m(i, k+). If this is the case, a speed component running transversely $v(i, k)_{trans}$ is determined for a voxel (i, k) 26, which speed component points from (i, k) to (i, k+) with a value which is proportional to the relative change in mass:

$$v(i, k)_{trans} \frac{m(i+1, k_+) - m(i, k_+)}{m(i, k) - m(i+1, k)}$$

It should be noted in this case that more than one voxel k+ must be found in which m(i, k+) has increased. An analog determination of the speed components running transversely $v(i, k)_{trans}$ is then carried out and the result of the overall speed vector is the sum of the individual components.

If m(i+1, k) is greater than m(i, k), then a flow running transversely into the voxel k (26) must have occurred. The adjacent voxels k– (26) are then checked for a fall of m(i+1, k–) relative to m(i, k–) and the corresponding speed component running transversely $v(i, k)_{trans}$ is determined for a voxel (i, k).

With said speed components running transversely $v(i, k)_{trans}$ it is for example possible to describe the flow into an aneurysm. For practical applications the discretization of the vascular 3D volume must be sufficiently fine and the time resolution of the 2D DSA sequences should be as high as possible, for example 100 fps (frames per second).

With reference to FIG. 5, the sequence according to the invention of an angiographic examination method for a vascular system of an object under examination 6 for the determination of flow characteristics inside vessels will now be described with the following steps:

Firstly, an acquisition of 4D angiography sequences takes place in a first method step S1). To this end, from projections of a rotational angiogram superimposition takes place by means of perspective back projection in a static 3D image of the vascular tree. In this situation, a time-resolved series of 3D data sets is produced; associated with each point in time in said series is a volume data set which represents the filling of the vascular tree with contrast agent at the respective point in time.

In a second method step S2) at least one relevant part of the vascular system, for example a vessel section 21, is identified in the 4D angiography sequences which can exhibit a vascular disorder or change. Said identification can take place manually or automatically in accordance with predefined criteria.

A centerline 22 is determined or calculated for said vessel section 21 in accordance with a third method step S3).

In a fourth method step S4), parallel lines 23 running parallel to the centerline 22 are ascertained which surround the centerline 22.

In a fifth method step S5), at positions (i, j) which can be determined or chosen along the centerline 22 perpendicular cross-sections 24 and 25 are specified which are intended to be used for determination of the blood flow.

In a sixth method step S6), voxels (i, j) 26 and 27 lying on the perpendicular cross-sections 24 and 25 are determined which lie in pairs in each case on the lines 22 or 23.

In accordance with a seventh method step S7), an ascertainment of bolus curves 11 takes place as a function of time for each voxel (i, j) 26 and 27 which intersects one of the cross-sections 24 or 25.

In accordance with an eighth method step S8), a time t is determined for each of said voxels (i, j) 26 and 27. Said time can be the maximum time 17 ($t_{max}$), the rise time 18 ($t_{wash\ in}$) of the wash-in phase and/or the fall time 19 ($t_{wash\ out}$) of the wash-out phase of the bolus curve 11.

In a ninth method step S9), the true Euclidean distance $\Delta D_E$ between voxels (i, j) 26 and 27 is measured at the positions i and j along the centerline 22 and the parallel lines 23.

In a tenth method step S10), said measured distance ($\Delta D_E$) is divided by the time difference $\Delta t = t_{(i+1)} - t_{(i)}$ in order to obtain the amplitude of a first speed component of the blood flow speed in each voxel (i, j) 26 and 27.

In accordance with an eleventh method step S11), a determination of second speed components, running transversely $v(i, k)_{trans}$, proportional to the relative change in mass takes place for each voxel(i, j) 26 and 27.

Finally, in a twelfth method step S12), the blood flow in the relevant part of the vascular system, the vessel section 21, is calculated on the basis of the speed components $$v(i, k)\text{trans} \frac{m(i+1, k_+) - m(i, k_+)}{m(i, k) - m(i+1, k)}.$$

The invention claimed is:

1. An angiographic method for examining a vascular system of an object under examination in order to determine flow characteristics inside vessels, comprising:
   S1) acquiring 4D angiography sequences;
   S2) identifying a relevant part of the vascular system in the 4D angiography sequences which could exhibit a vascular disorder or vascular change;
   S3) determining a centerline for the identified relevant part;
   S4) ascertaining of parallel lines which run parallel to the centerline and surround the centerline;
   S5) specifying perpendicular cross-sections at least at positions which can be determined or chosen along the centerline;
   S6) determining voxels lying on the perpendicular cross-sections;
   S7) ascertaining bolus curves as a function of time for each voxel which intersects one of the cross-sections;
   S8) determining a time for each of said voxels;
   S9) measuring of the true Euclidean distance between voxels at the positions along the centerline and the parallel lines;
   S10) dividing said measured distance by the time difference in order to obtain the amplitude of a first speed component of the blood flow speed in each of said voxels;
   S11) determining second speed components, running transversely, proportional to the relative change in mass of the blood in the voxels, for each of said voxels and
   S12) calculation of the blood flow in the relevant part of the vascular system on the basis of the speed components.

2. The angiographic examination method as claimed in claim 1, wherein the acquisition of the 4D angiography sequences takes place in accordance with step S1) from rotational angiography projections which are superimposed by means of perspective back projection in a static 3D image of the vascular tree.

3. The angiographic examination method as claimed in claim 1, wherein the calculation of the second speed components, running transversely occurs in accordance with S11) according to the formula:

$$v(i,k)\text{trans} \frac{m(i+1,k_+) - m(i,k_+)}{m(i,k) - m(i+1,k)}.$$

4. The angiographic examination method as claimed in claim 2, wherein the calculation of the second speed components, running transversely occurs in accordance with S11) according to the formula:

$$v(i,k)\text{trans} \frac{m(i+1,k_+) - m(i,k_+)}{m(i,k) - m(i+1,k)}.$$

5. The angiographic examination method as claimed in claim 1, wherein accordance with S8) the time is the maximum time, rise time of the wash-in phase and/or fall time of the wash-out phase of the bolus curve.

6. The angiographic examination method as claimed in claim 2, wherein accordance with S8) the time is the maximum time, rise time of the wash-in phase and/or fall time of the wash-out phase of the bolus curve.

7. The angiographic examination method as claimed in claim 3, wherein accordance with S8) the time is the maximum time, rise time of the wash-in phase and/or fall time of the wash-out phase of the bolus curve.

8. The angiographic examination method as claimed in claim 1, wherein after calculation of the first speed component for each voxel in accordance with S10) all adjacent voxels are examined as to whether relative changes exist in the masses m(i+1, k+) to m(i, k+), and only then is the transversely running speed component, which exhibits a value proportional to the relative change in mass, determined in order to determine second speed components in accordance with S11) for a voxel.

9. The angiographic examination method as claimed in claim 2, wherein after calculation of the first speed component for each voxel in accordance with S10) all adjacent voxels are examined as to whether relative changes exist in the masses m(i+1, k+) to m(i, k+), and only then is the transversely running speed component, which exhibits a value proportional to the relative change in mass, determined in order to determine second speed components in accordance with S11) for a voxel.

10. The angiographic examination method as claimed in claim 3, wherein after calculation of the first speed component for each voxel in accordance with S10) all adjacent voxels are examined as to whether relative changes exist in the masses m(i+1, k+) to m(i, k+), and only then is the transversely running speed component, which exhibits a value proportional to the relative change in mass, determined in order to determine second speed components in accordance with S11) for a voxel.

* * * * *